United States Patent [19]

Headley

[11] Patent Number: 4,983,158

[45] Date of Patent: Jan. 8, 1991

[54] PLASMAPHERESIS CENTRIFUGE BOWL

[75] Inventor: Thomas D. Headley, Wellesley, Mass.

[73] Assignee: Haemonetics Corporation, Braintree, Mass.

[21] Appl. No.: 436,963

[22] Filed: Nov. 15, 1989

Related U.S. Application Data

[63] Continuation of Ser. No. 232,544, Aug. 15, 1988, abandoned, which is a continuation of Ser. No. 888,764, Jul. 22, 1986, abandoned.

[51] Int. Cl.⁵ .................................................. B04B 7/02
[52] U.S. Cl. ......................................... 494/41; 494/38; 494/64; 604/6
[58] Field of Search ..................... 494/38, 40, 41, 43, 494/48, 60, 64, 65, 73, 76, 77, 80; 604/6

[56] References Cited

U.S. PATENT DOCUMENTS

| | | | |
|---|---|---|---|
| 447,530 | 3/1891 | Wahcin | 494/43 |
| 528,683 | 11/1894 | Ohlsson | 494/64 |
| 754,909 | 3/1904 | Springer | 494/64 X |
| 886,393 | 5/1908 | Morgan | 494/64 |
| 1,603,726 | 10/1926 | Thomsen | 494/64 |
| 3,125,516 | 3/1964 | Kaldewey | 494/43 |
| 3,675,846 | 7/1972 | Drucker | 494/45 |
| 3,771,353 | 11/1973 | Jenkins | 494/38 |
| 3,899,128 | 8/1975 | Joyce | 494/38 |
| 4,059,108 | 11/1977 | Latham, Jr. | 604/6 |
| 4,086,924 | 5/1978 | Latham, Jr. | |
| 4,140,268 | 2/1970 | Lacour | 494/41 |
| 4,152,270 | 5/1979 | Cornell | 494/38 |
| 4,300,717 | 11/1981 | Latham, Jr. | |
| 4,718,888 | 1/1988 | Darnell | 494/38 X |

FOREIGN PATENT DOCUMENTS 606630  5/1978  U.S.S.R. .................. 494/38

Primary Examiner—Harvey C. Hornsby
Assistant Examiner—Stephen F. Gerrity
Attorney, Agent, or Firm—Hamilton, Brook, Smith & Reynolds

[57] ABSTRACT

An improved disposable plasmapheresis centrifuge bowl is described comprising a rotary seal enclosing an aperture in a one-piece seamless bowl body through which various core members may be inserted.

21 Claims, 3 Drawing Sheets

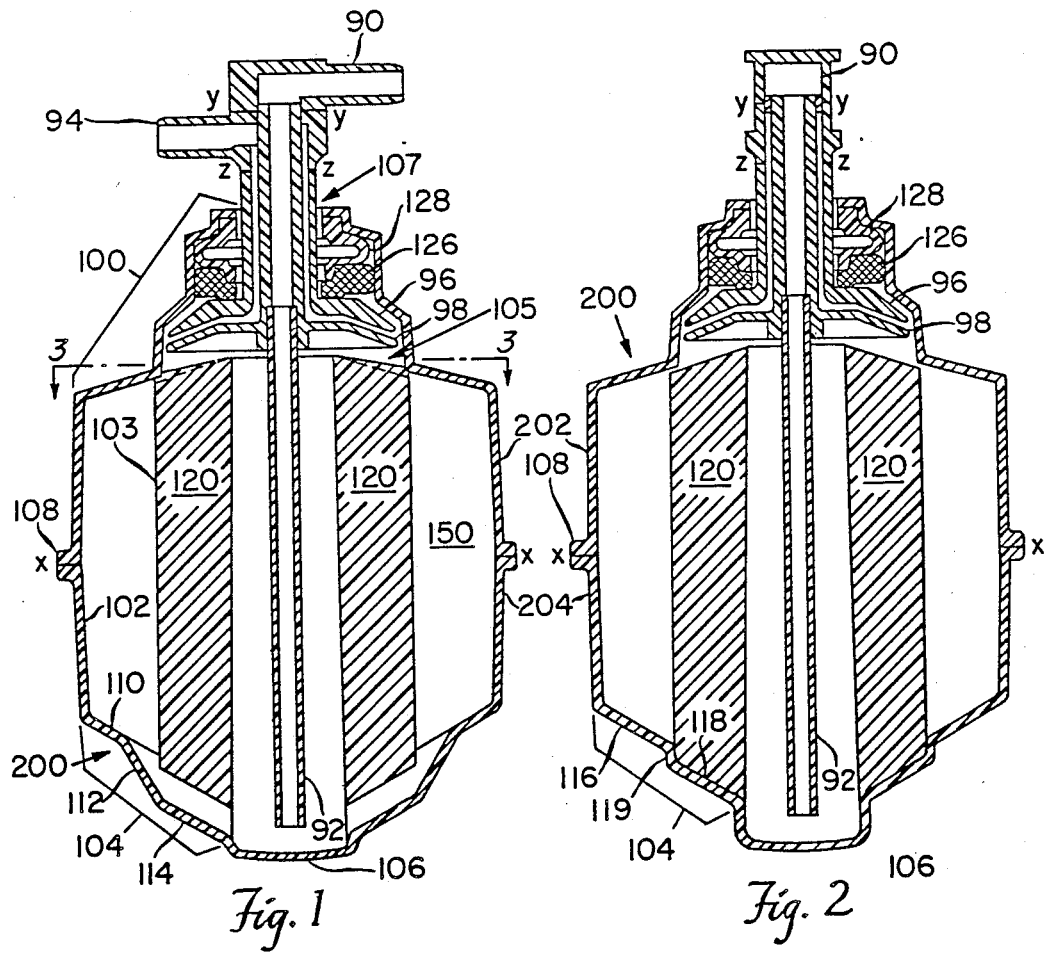
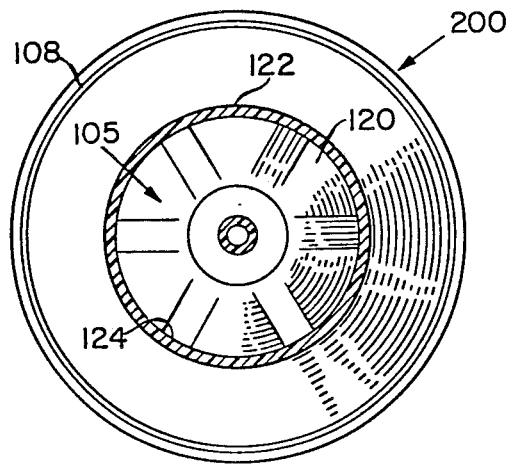
Fig. 1
Fig. 2
Fig. 3

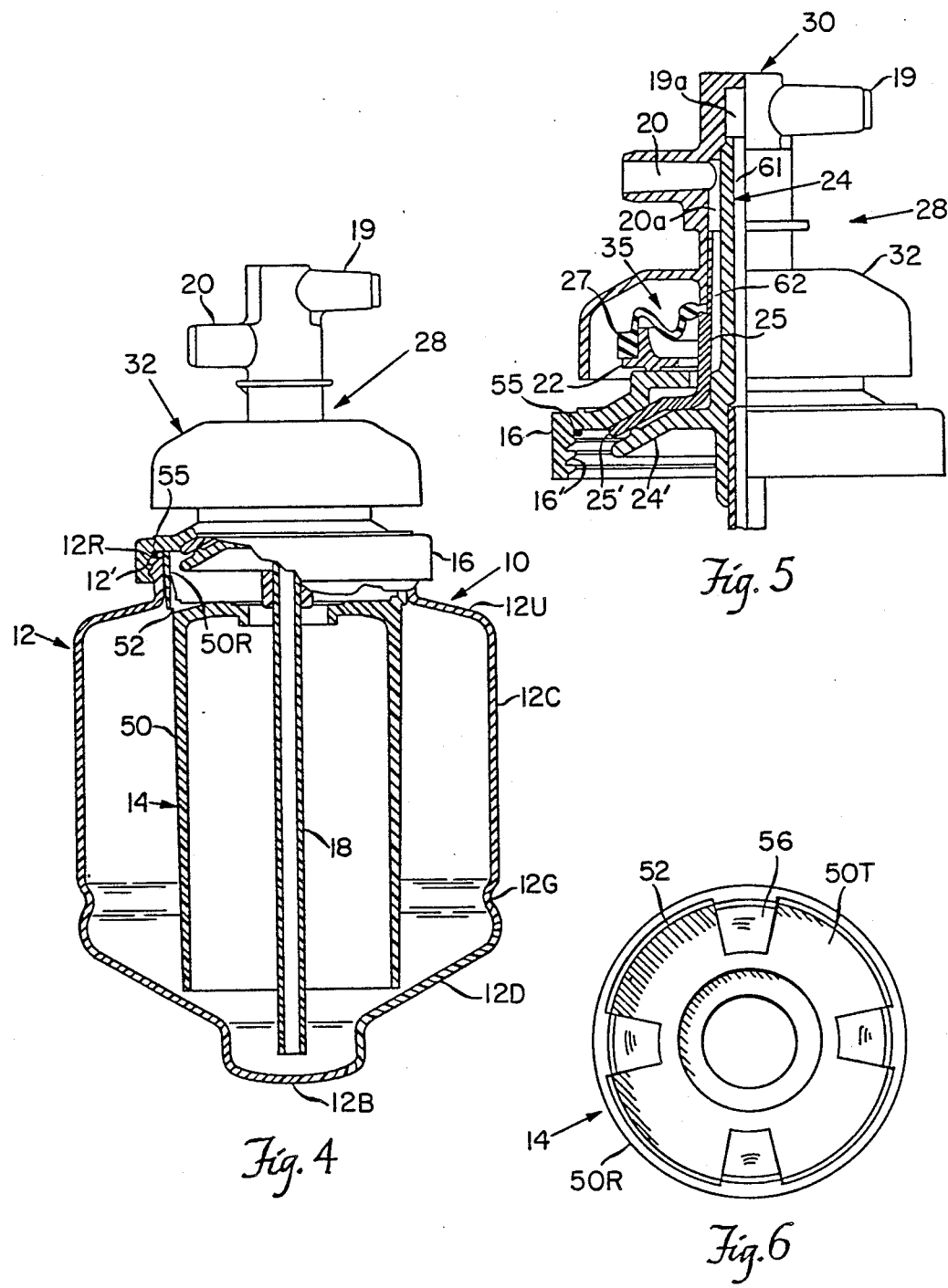

4,983,158

PLASMAPHERESIS CENTRIFUGE BOWL

This is a continuation of application Ser. No. 07/232,544 filed on Aug. 15, 1988, (now abandoned) which is Continuation of Ser. No. 06/888,764 filed July 22, 1986 (now abandoned).

DESCRIPTION

1. Technical Field

This invention relates to blood processing and, more specifically, plasmapheresis.

2. Background Art

A plasmapheresis process is described in U.S. Pat. No. 4,086,924 issued May 2, 1978 to Allen Latham, Jr. In this plasmapheresis process, whole blood is withdrawn from a donor using a phlebotomy needle and pressure cuff and mixed with anticoagulant and transported by a blood pump to a plasmapheresis centrifuge bowl 10 in which the whole blood is separated into a plasma and non-plasma component.

The centrifuge bowl 200 is described in connection with FIGS. 4 and 5 of U.S. Pat. No. 4,086,924, which are reproduced herein as FIGS. 1, 2 and 3 and labelled "Prior Art". As shown therein, the centrifuge generally comprises a multi-piece feed tube and seal assembly with a first transverse central input port 90 leading to a longitudinal feed tube stem 92 through which whole blood is introduced into the bottom 106 of the centrifuge bowl 200.

A second transverse peripheral port 94 is provided to allow separated plasma component to flow out of the centrifuge bowl 200. A channel leading to peripheral port 94 is formed between upper skirt 96 and lower skirt 98, which extend outwardly from a point approximately opposite where the central port 90 joins feed tube stem 92.

The outlet channel formed between upper and lower skirts 96 and 98, respectively, continues into an annular coaxial channel around the periphery of the longitudinal extension of central port 90 until it joins peripheral port 94.

An elastomeric bellows 128 forms a spring member which urges carbon ring seal 126 against skirt 96 forming a rotary seal therebetween.

Central port 90, feed tube stem 92, peripheral port 94 and skirts 96 and 98 are generally manufactured by molding or extrusion techniques using blood compatible plastic, such as styrene, ABS, polycarbonate, polyethylene, polyurethane, etc. The ports and skirts are part of a feed tube assembly which is coaxial to and remains stationary while the centrifuge bowl rotates about its longitudinal axis.

The centrifuge bowl body 200 is of two piece construction formed of two integrally molded pieces, an upper piece 202 and lower piece 204, which are joined at approximately the mid-point, where a raised joint 108 is provided so that the upper and lower halves of the bowl, which were separately injection-molded, may be joined by welding. A molded series of outer wall members comprising an inclined upper wall member, shown generally at 100, a substantially vertical central wall member 102, and a lower steeply inclined wall member 104, and a recessed bottom wall member 106 define the exterior walls of the centrifuge bowl chamber.

A tubular core 120 defines a separation channel 150 between the outer core wall 103 and the inner longitudinal walls of the bowl body wall. As shown in the planar view of FIG. 3, the core is provided with vanes 122 which have steps 124 at the extremities, which are used to accurately position the core coaxially by seating part of the upper housing 124 against the vanes. When they are seated, vanes 122 serve to provide a flow channel or opening from the sedimentation area along the longitudinal length of the core wall 103, leading to the outlet channel formed between skirts 96 and 98.

Weld lines X—X, Y—Y and Z—Z have been added to FIGS. 1 and 2 of the drawings to show how the individual parts and assemblies of the prior art bowl body 200 are joined together and assembled. As may be seen therefrom, the lower portion and upper portion of the feed tube and seal assembly is welded at two places, Z—Z and Y—Y, after the lower portion is inserted through a first large intermediate opening 105 and a second smaller opening 107 in upper bowl body piece 202. Next, core 120 is snapped in place on upper piece 202 by means of vanes 122 which seat on the upper piece. Finally, lower piece 204 is placed over the core 120 abutting joint 108 at X—X and is welded in place.

Apart from the overall labor intensive complexity of the above procedure, several basic problems exist in the prior art bowl construction above described. First, the weld at 108 about the periphery of the bowl body is subjected to the greatest possible centrifugal forces when the bowl is in operation since it is located at the furthest radial point from the bowl axis. Rupture of the weld at this juncture is a chief cause of bowl failure. Secondly, the bowl construction does not permit testing of the seal and feed tube assembly until it is permanently integrated with the bowl. Thus, if a defect is found in the assembly, the complete assembly must be scrapped.

Accordingly, a need exists for a more reliable, easier to assemble, centrifuge bowl capable of mass production with a minimum amount of labor and in which the seal and feed tube assembly can be separately tested.

DISCLOSURE OF THE INVENTION

The method and apparatus of the present invention comprises a disposable centrifuge rotor or bowl formed of two basic items. The first is a rotary seal and header assembly; the second, a unitary, integral, seamless, one piece bowl body. A third optional element comprises, a series of core member or members capable of being used in a standard bowl body for different separation processes. The seal and header assembly is capable of being assembled on an automatic machine. The bowl body is adapted to be manufactured by blow molding or injection blow molding and the core member, or members, by injection molding or other forming process.

The integral bowl body is adapted for rotation about its longitudinal axis. A single aperture is provided at one end of the bowl body concentric with the longitudinal axis of the bowl body. Core members of various configurations are adapted to be insertable through the aperture in the bowl body concentric with the longitudinal axis of the bowl.

The seal and header assembly has a first seal or crown member which mates with the outer body wall of the bowl member about the periphery of the bowl body aperture to affix the seal and header assembly to the bowl body. The seal and header assembly is formed of a header with input and output ports, and a feed tube coupled to the inlet port which extends within the core member concentric with the longitudinal axis of the bowl body and terminating a short distance from the lower wall of the bowl body.

An effluent tube is formed about the inner feed tube assembly with a narrow channel provided therebetween for flow of effluent, for example, plasma, to the outlet port. A second seal member is formed about the periphery of the effluent tube to form a rotary seal over the first seal member which permits the inner and outlet ports to remain stationary while the bowl rotates about its central axis.

The entire centrifuge rotor thus described can be assembled in a matter of seconds after the outside seal and header assembly has been assembled by automated assembly techniques. A selected core member is inserted into the aperture in the unitary bowl body. Next, the seal and header assembly is placed over the aperture and the feed tube inserted into a concentric opening in the core until the first seal or crown is mateably engaged with the outer wall of the aperture and a seal is formed therebetween.

BRIEF DESCRIPTION OF THE DRAWINGS

FIGS. 1 and 2 are respectively front and side cross-sectional views of the centrifuge bowl described in U.S. Pat. No. 4,086,924 and labelled "Prior Art".

FIG. 3 is a transverse cross-sectional view along line 3—3 of FIG. 1 of the prior art.

FIG. 4 is a partial cutaway side cross-sectional view of the centrifuge bowl of the present invention.

FIG. 5 is a partial cut-away sectional view of the feed tube assembly of FIG. 4.

FIG. 6 is a sectional view along the lines 6—6 of FIG. 4 showing only the end view of the core 14.

BEST MODE OF CARRYING OUT THE INVENTION

Figure 6A:
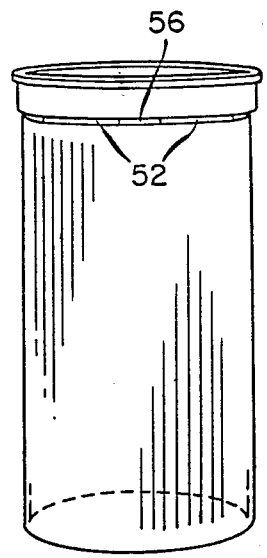
FIG. 6A is a perspective view of the core 14 showing the slots 52 in more detail.

Referring now to FIGS. 4-6, a preferred embodiment of the invention will now be described in connection therewith. As may be seen therein, the apparatus of the invention comprises a disposable centrifuge rotor, or bowl, 10. The bowl comprises: a seal and header assembly, shown generally at 28 (FIG. 5), a one-piece, seamless, integral bowl body shown generally at 12 (FIG. 4) and a core member 14 (FIG. 6 and FIG. 4).

The seal and header assembly 28 is capable of being assembled utilizing automatic machine techniques. The seal and header assembly is comprised of a header 30, an effluent tube 25, a feed tube assembly 24, and a rotary seal 35 formed of a seal ring 22, and a flexible member 27 and an outside seal member or crown 16.

The header 30 comprises an integral formed member having a transverse inlet bore 19 extending into a longitudinal passageway 19a coupled to the inner bore 61 of feed tube assembly 24 and, in turn, to feed tube stem 18, thus forming an inlet path for anticoagulated whole blood to enter the interior of centrifuge bowl body 12.

Header 30 also includes an outlet port, or bore 20, which extends transversely into a peripheral channel 20a extending in parallel relationship with the feed tube assembly 24 and into an outlet passageway 62. A shield portion 32 formed on header 30 extends over the rotary seal 35.

Feed tube assembly 24 is formed with an integral skirt 24' disposed adjacent a complimentary effluent tube skirt 25' formed on effluent tube 25.

The rotary seal 35, as mentioned above at page 7, lines 24-28 permits the inlet bore on port 19 and outlet bore on part 20 to remain stationary while the bowl is rotating, and is formed of a two-piece secondary seal ring which consists of flexible outside sealing member 27, which is affixed about its outer periphery to the periphery of molded ring seal 22. Ring seal 22 forms a rotary seal with a seal crow 16 having internal screw threads 16', about the internal periphery thereof, and is provided with a central opening through which effluent tube 25 extends. The seal crown threads 16' mate with the external threads 12' of bowl body 12. Thus, seal crown 16 rotates with the bowl body whereas molded seal ring 22 is affixed to the non-rotatable stationary inner and outlet ports. The inner periphery of flexible member 22 is joined to the effluent tube.

The header and seal assembly 28, as thus described, is formed and assembled as an individual entity and is inserted through an upper central opening in bowl body 12, as shown in FIG. 4 and mated with external threads 12' formed on the periphery of bowl body 12 after core member 14 has been inserted through said opening and fixed in place within the bowl body 12, as will be subsequently described.

The bowl body 12 is an integral body adapted to be manufactured by blow molding or injection blow molding and may be formed of a suitable plastic, such as transparent styrene or equivalent.

The bowl body is formed of an upper ring portion 12R, an upper diagonal portion 12U, a middle central portion 12C, a lower diagonal portion 12D and a bottom cross portion 12B. Screw threads 12' are formed on the outer surface of ring portion 12R and an opening extends longitudinally from the inner surface of the ring portion 12R into the main portion of the bowl body 12. A groove is formed about the periphery of the bowl at 12G to form a holding surface for a centrifuge rotor chuck (not shown).

An O-Ring gasket 55 is disposed on an inner peripheral shoulder of crown member 16 adjacent screw threads 16'. When member 16 is threaded onto bowl body 12, gasket 55 is compressed against the upper wall of ring 12R forming a liquid tight seal.

A cylindrical walled core 14 is adapted to be inserted into the upper opening in bowl body 12 through the opening in ring portion 12R. Core 14 is an integral member having a cylindrical outer wall 50 extending longitudinally and coaxial to the axis of bowl body 12. An upper ring portion 50R of core 14 is adapted to abut the inner wall of the ring portion 12R of bowl body 12 when the core is inserted into the upper opening of the bowl body 12.

Four L-shaped reinforcing tabs 56 are formed on the top wall 50T of core 14 to reinforce the ring portion 50R. Four peripheral slots 52 extend along the periphery of the core 14 at the juncture between the ring portion 50R and the cylindrical wall 50, as shown more clearly in FIG. 6A. These slots 52 provide a passageway for the exit of effluent, such as plasma, which has been separated from the whole blood by the operation of the centrifuge plasmapheresis process within the bowl body 12.

This operation may be described generally as follows: Whole blood is coupled from inlet port 19 through the longitudinal passageway in feed tube assembly 24 to the bottom of the spinning centrifuge bowl. The heavier red blood cells are forced radially outwardly from the central axis and are retained on the inner bowl wall along the main or central body portion 12C of the bowl. The lighter, less dense plasma is captured on the outer surface of cylindrical wall 50 and allowed o exit through the slots 52 at the top wall 50T of core 14 whereupon they pass through the channel between skirts 24' and 25' into the passageway 62 and out the outlet port 20 of header 30.

As mentioned previously, one of the advantages of the present invention is that the outside seal and header assembly 28 may be separately tested. For example, the assembly may be fastened to a test bowl body and checked under pressure for leaks, etc. Similarly, the bowl body 12 may be separately checked for leaks while attached to a test fixture. After testing of each, they may be assembled manually or with the use of automatic machinery.

Figure 7:
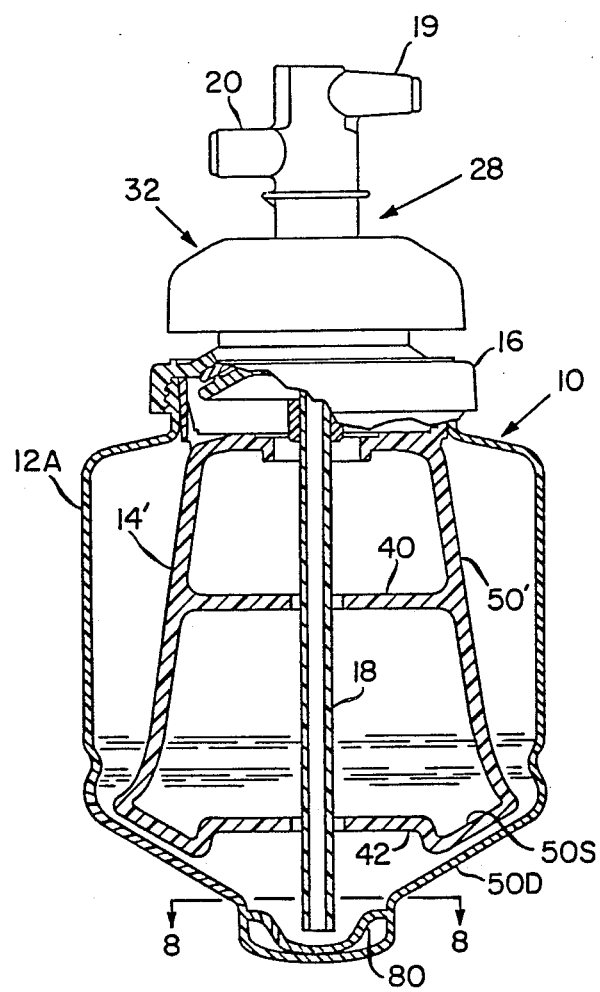
FIG. 7 is a partial cutaway side cross-sectional view of the centrifuge bowl of the invention showing an alternate embodiment of the core member.

In the alternate embodiment shown in FIG. 7, the bowl body 12A and header and seal assembly 28 are substantially similar to that previously described. However, the core labelled 14' is flared at the lower extremity and is formed of semi-rigid plastic material, such as polyvinylchloride (PVC) to allow the flared core to be inserted through the upper opening in the bowl body by deflecting the longitudinal wall 50'. This results in a core body having skirts 50S extending parallel to the diagonal walls 50D of the bowl body. This skirted core configuration is similar to that shown in U.S. Pat. No. 4,300,717 and enables different blood flow patterns to be formed within the bowl.

Figure 8:
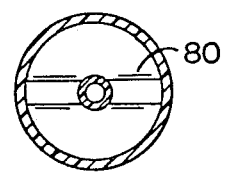
FIG. 8 is a sectional view taken along lines 8—8 of FIG. 7.

FIG. 8 shows the lower bowl body details of the alternate embodiment of FIG. 7 in which channels 80 are formed in the bowl body 12' during the molding process to facilitate flow of blood from the center of the bowl to the sides in a predetermined pattern.

Figure 9:
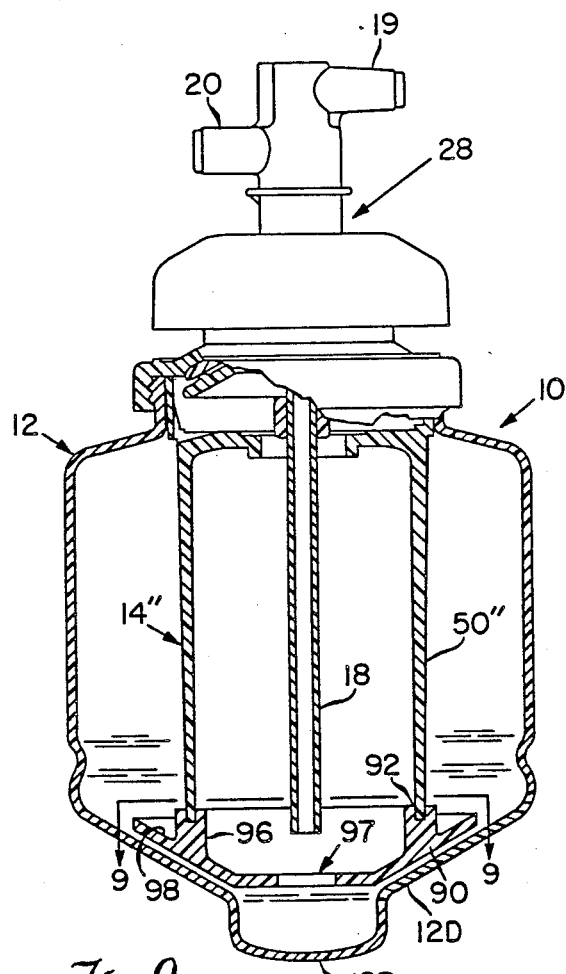
FIG. 9 is a partial cross-sectional view of yet another embodiment of the invention showing a two-piece core construction.
Figure 10:
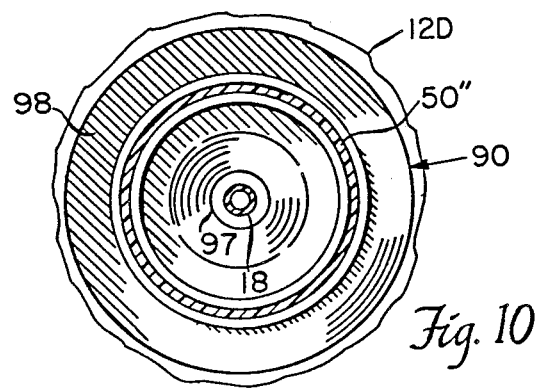
FIG. 10 is a detailed view taken along line 9—9 of FIG. 9.

FIGS. 9 and 10 depict an alternate two-piece core embodiment in which the core member 14" is comprised of a generally cylindrical hollow walled core, as in FIG. 4, but includes a disc-like member 90 which provides a flared wall portion 98 adjacent diagonal bowl wall 12D. Member 90 is made of semi-rigid plastic which can be compressed to allow it to pass through the top opening in the bowl body. Circular grooves formed around protrusions 96 on member 90 permit cylindrical core wall 50" to mate with member 90 after the core is inserted into the bowl body. The grooves 92 form a press-fit holding the two pieces 90 and 50' together during rotation of the bowl 10. Aperture 97 permits whole blood from feed tube stem 18 to enter the bottom of the bowl body 12B.

EQUIVALENTS

Those skilled in the art will recognize that there are many equivalents to the specific embodiments described herein. Such equivalents are intended to be encompassed within the scope of the following claims.

I claim:
1. A disposable centrifuge rotor comprising:
(a) an integral seamless, plastic, optically transparent, unitary bowl body having an inner wall and an outer wall and rotatable about an axis and having a main body portion extending concentric to said axis, with upper and lower body portions extending radially inwardly toward said axis and a single aperture therein through said upper body portion which aperture is smaller than the inner wall diameter of the bowl body transverse said axis at said main body portion;
(b) a rotary seal assembly affixed to said bowl body and covering said aperture and comprising a non-rotatable seal ring and a rotatable seal ring, with the rotatable seal ring affixed to said bowl body at the aperture and fixed inlet and outlet ports affixed to said non-rotatable seal ring and in fluid communication with the interior of the bowl body, the inlet port extending along the bowl axis to the lower body portion of the bowl body; and
(c) a separate rigid core member directly abutting said bowl body and detached from said rotary seal assembly having an outer diameter smaller than said aperture and rotatable with said bowl body and comprising a cylindrical core extending concentric to the bowl body axis along a substantial length of the inlet port.

2. The rotor of claim a wherein the core member has an outer diameter small enough to enable passage through said aperture.

3. The rotor of claim 2 wherein the aperture has a periphery and an O-ring is disposed between the seal and bowl body about the periphery of the aperture.

4. A disposable blood processing centrifuge rotor comprising:
(a) a seamless plastic, unitary, optically transparent, molded bowl body having an inner wall and an outer wall and rotatable about its longitudinal axis and having a main body portion extending concentric to said axis, with upper and lower body portions extending radially inwardly toward said axis and a single closeable aperture concentric with said axis and located at said upper body portion and wherein the aperture has a periphery and wherein the size of the aperture is less than the inner wall diameter of said bowl body transverse said longitudinal axis at said main body portion;
(b) a separate core member directly abutting and rotatable with said bowl body having a main substantially rigid generally tubular body extending longitudinally concentric with said axis, said tubular body having an inner diameter and an outer diameter, the outer diameter of said main tubular body being equal to or not greater than the inner diameter of said aperture and having an open center extending within said bowl from said aperture about said axis;
(c) a rotary seal assembly detached from said core member for providing fluid communication between the interior of the bowl body and non-rotating input and output ports external to the bowl body and having a cover for sealing said seal assembly to the bowl body about the periphery of said aperture and said inlet port extending along said longitudinal axis to the lower body portion of the bowl body.

5. The rotor of claim wherein the open center of the core member extending within the bowl has an outer diameter smaller than the aperture diameter.

6. A disposable centrifuge blood processing rotor comprising:

(a) an integral seamless, optically transparent, unitary bowl body having an inner wall and an outer wall and rotatable about its longitudinal axis and of generally tubular shape with a smooth longitudinally extending tubular body wall surface and upper and lower radially inclined wall surfaces and wherein a diameter of the bowl body transverse the longitudinal axis extending at the tubular body wall surface is a maximum, and having a single aperture concentric with said longitudinal axis located at said upper wall surface of the bowl body, said aperture having a periphery and being smaller than the diameter of the inner wall of said bowl body taken transverse said axis at said tubular body wall surface;

(b) a core member directly abutting and rotatable with said bowl body and having an internal central bore concentric with said bowl body axis; and a rotary seal assembly for sealing said aperture affixed to the outer wall about the periphery of said aperture and separate from said core member and having a non-rotary effluent port and input port in fluid communication with the interior of said bowl body.

7. The disposable centrifuge rotor of claim 6 wherein said rotor separates whole blood entering said input port into whole blood constituents which exit said effluent port including a peripheral opening formed at least partially about the periphery of said core member for permitting exit of said separated whole blood constituents from said bowl body to said effluent port.

8. A disposable centrifuge rotor for centrifuging whole blood to separate such blood into components, said whole blood being supplied from an external source comprising:

(a) an integral, seamless, unitary, optically transparent bowl body having an inner wall and an outer wall and adapted for rotation about an axis and having a smooth outer wall extending longitudinally coaxial to said axis along a longitudinal length of said bowl body and upper and lower walls extending radially inwardly toward said axis and having a single aperture, said aperture having a diameter less than a diameter of the inner wall of said bowl body therein through said upper wall of the bowl body, as measured transverse said outer wall; and (b) a rotary seal assembly for sealing said aperture having a non-rotatable seal ring and a rotatable seal ring with the rotatable seal ring affixed to said bowl body;

(c) non-rotatable entry and exit ports coupled to said non-rotatable seal ring and fluidly coupled to said bowl body through said aperture for admitting said whole blood into said bowl body; and (d) a core member insertable through said aperture and directly abutting and rotatable with said bowl body but separate and distinct from said rotary seal assembly.

9. The rotor of claim 12 wherein the core member has a peripheral dimension smaller than said aperture.

10. The rotor of claim 8 wherein the core member comprises a rigid member having an outer diameter small enough to enable passage through said aperture.

11. A disposable blood processing centrifuge rotor comprising:

(a) an integral, seamless, unitary plastic, molded, bowl body having an inner wall and an outer wall and rotatable about an axis and having a single aperture therein through an upper wall of the bowl body with a radially outwardly inclined upper wall section, a vertically extending midsection and a radially inwardly inclined lower section converging at a bottom wall and wherein a diameter of the aperture is smaller than a diameter of the inner wall of the bowl body taken transverse the midsection;

(b) a rotary seal assembly affixed to said bowl body and covering said aperture for providing non-leaking fluid communication between a fixed input port and a fixed output port and the interior of said bowl body while said bowl body is rotating and wherein fluid is introduced from said input port to a central location at the bowl body axis adjacent said lower section; and (c) a core member assembly abutting said bowl body at the aperture and detached from said rotary seal assembly and which is inserted through said aperture prior to its being covered by said seal assembly, said core member assembly comprising a generally cylindrical hollow walled core extending longitudinally along the bowl axis and a flexible disc-like member extending laterally across the interior of said bowl body near the lower section for guiding fluid, introduced at the central axial location adjacent said lower wall, radially outwardly for passage to said output port.

12. The rotor of claim 1 wherein the hollow walled core is rigid and has a distal end near the lower section and an outer diameter small enough to enable passage through said aperture and the disc-like member has a greater diameter than the aperture and which disc-like member is sufficiently compressible to pass through said aperture and thereafter expand and abut the distal end of said rigid member.

13. A disposable centrifuge blood processing rotor comprising:

(a) a seamless bowl body with an inner wall diameter and an outer wall diameter sidewall said body being rotatable about its longitudinal axis and having a single closeable aperture located in the top wall with a diameter smaller than the inner wall diameter of said sidewall, said aperture being concentric with said axis;

(b) a core rotatable with said bowl body and insertable through said aperture comprising a core member concentric with said axis and having an open walled cylinder longitudinally extending within said bowl body from said aperture about said axis and a disc-like member extending radially transverse said axis in proximity with said inclined wall and having a transverse diameter larger than said diameter of said aperture abutting a lower portion of the cylinder; and (c) a rotary seal assembly separate from said core for providing fluid communication between the interior of said bowl body and a stationary location exterior of said bowl body while said bowl body is rotating, said seal assembly having a cover for sealing said seal assembly to the outer body wall about the periphery of said aperture and a conduit means for introducing fluid into said bowl body at a central axial location closely opposite said bottom wall.

14. The rotor of claim 13 wherein the open walled cylinder of the core member extending within the bowl has an outer diameter equal to or smaller than the aperture diameter and an inlet fluid conduit extends along the axis of the bowl body to the bottom of the bowl body and the disc-like member has an outer diameter larger than the aperture diameter but is sufficiently flexible as to be insertable through said aperture, yet retain its previous shape after insertion to vary the flow pattern of fluid admitted to the bottom of the bowl body from the inlet conduit.

15. The rotor of claim 13 wherein the core is of two-piece construction and one piece is the core member and the other piece is the transverse member.

16. A disposable centrifuge blood processing rotor for separating whole blood into components and wherein said whole blood is supplied from an external source comprising:
   (a) a bowl body having a top wall, a bottom wall, a main sidewall with an inner wall diameter and an outer wall diameter and an inclined sidewall extending between the bottom wall and main sidewall, said body adapted for rotation about its longitudinal axis and having a single aperture located in the top wall concentric with said axis and wherein a diameter of said aperture is smaller than an inner wall diameter of the bowl body transverse the longitudinal axis at the main sidewall;
   (b) a two-piece core member rotatable with said bowl body and abutting said bowl body at the aperture and having an internal central bore concentric with said bowl body axis said two pieces comprising:
      (i) a first piece having a cylindrical wall extending longitudinally from the aperture into the bowl body, and
      (ii) a second generally disc-like piece extending radially transverse the axis of said bowl body close to the inclined sidewall; and
   (c) a rotary seal assembly separate from said core member and affixed to the top wall about the aperture for providing non-leaking fluid communication between a stationary effluent port and input port and the interior of said bowl body while the bowl body is rotating and wherein the inlet port introduces whole blood at the bowl body while the effluent port permits exit of separated blood component.

17. The disposable centrifuge rotor of claim 16 wherein the bowl body is of one-piece construction and including a peripheral slit extending at least partially about the periphery of said core member for permitting exit of separated whole blood constituents from said bowl body to said effluent port and wherein the diameter of the cylindrical wall of the first piece is less than or equal to the diameter of the aperture and the transverse diameter of the second piece is greater than the diameter of the aperture.

18. The rotor of claim 17 wherein the second piece is semi-rigid.

19. The rotor of claim 16 wherein the bowl body is of one-piece seamless construction.

20. In a blood processing centrifuge rotor formed of a bowl body with a top wall, a generally cylindrical side wall and a radially downwardly inclined wall extending from said side wall and joining a transverse bottom wall, said top wall having an opening of diameter D1 covered by a rotary seal having an input port and an output port for providing fluid communication of blood processing fluids respectively into and out of the interior of said bowl body while said bowl body is rotating and a feed tube coupled to said input port for introducing blood processing fluid into the bowl body interior near the bottom wall; the improvement comprising:
   (a) a generally cylindrical walled core having a diameter D2 less than or equal to D1 insertable in said opening with the space between said walled core and said side wall forming a blood processing separation region; and
   (b) an annular semi-rigid disc-like member having an outer diameter D3 greater than D1 extending radially across said bowl body near said inclined wall for coupling blood processing fluid, introduced near the interior of the bottom wall, to a radially outer periphery of said separation region.

21. The rotor of claim 20 wherein the bowl body is an integral one-piece seamless bowl.

* * * * *

UNITED STATES PATENT AND TRADEMARK OFFICE
CERTIFICATE OF CORRECTION

PATENT NO. : 4,983,158

DATED : January 8, 1991

INVENTOR(S) : Thomas D. Headley

It is certified that error appears in the above-identified patent and that said Letters Patent is hereby corrected as shown below:

Col. 6, line 24, delete "a" and insert ---1---.

Col. 6, line 51, delete "equal to or".

Col. 6, line 64, after "claim", insert ---4---.

Col. 7, line 18, after "axis; and", insert new paragraph ---(c)---.

Col. 8, line 39, after "body", delete "with an inner wall diameter and an outer wall diameter", insert ---having top and bottom walls and a sidewall with an inner wall diameter and an outer wall diameter, and an inclined wall extending radially upwardly from said bottom wall to said---.

Col. 9, line 42, after "the" (first occurrence) insert ---longitudinal axis near the bottom wall of the---.

Signed and Sealed this

Fourth Day of August, 1992

Attest:

DOUGLAS B. COMER

*Attesting Officer*  *Acting Commissioner of Patents and Trademarks*